(12) United States Patent
Friedman et al.

(10) Patent No.: US 8,047,997 B2
(45) Date of Patent: Nov. 1, 2011

(54) NON-INVASIVE BLOOD PRESSURE MONITOR APPARATUS AND SYSTEM

(75) Inventors: Bruce A. Friedman, Tampa, FL (US); Richard Medero, Tampa, FL (US); John P. Clemmons, Tampa, FL (US)

(73) Assignee: General Electric Company, Schenectady, NY (US)

( * ) Notice: Subject to any disclaimer, the term of this patent is extended or adjusted under 35 U.S.C. 154(b) by 1100 days.

(21) Appl. No.: 11/845,425

(22) Filed: Aug. 27, 2007

(65) Prior Publication Data

US 2009/0062663 A1    Mar. 5, 2009

(51) Int. Cl.
*A61B 5/02* (2006.01)

(52) U.S. Cl. ........ 600/490; 600/493; 600/494; 600/495; 600/499; 606/202

(58) Field of Classification Search .................. 600/485, 600/490, 495, 587; 606/203, 202
See application file for complete search history.

(56) References Cited

U.S. PATENT DOCUMENTS 4,605,010 A * 8/1986 McEwen ....................... 600/499
* cited by examiner

*Primary Examiner* — Miranda Le
*Assistant Examiner* — Scott Gonzalez
(74) *Attorney, Agent, or Firm* — Andrus, Sceales, Starke & Sawall, LLP

(57) ABSTRACT

A non-invasive blood pressure monitoring system is disclosed herein. The non-invasive blood pressure monitoring system includes a pressure cuff comprising a resistive portion and a conductive portion aligned with the resistive portion. The non-invasive blood pressure monitoring system also includes a controller operatively connected to the pressure cuff. The controller is adapted to estimate the circumference of the pressure cuff based on the position of the conductive portion relative to the resistive portion.

17 Claims, 3 Drawing Sheets

NON-INVASIVE BLOOD PRESSURE MONITOR APPARATUS AND SYSTEM

BACKGROUND OF THE INVENTION

Conventional non-invasive blood pressure (NIBP) monitoring systems generally inflate a pressure cuff above the patient's systolic pressure and measure oscillations in the cuff as the cuff is deflated. The pressure cuff is wrapped around a limb and secured thereto with a fastening mechanism such as, for example, Velcro. After wrapping and securing the pressure cuff to a limb, a cuff bladder is inflated with air in order to apply pressure. The oscillations monitored by the NIBP system are transmitted through the air contained within the cuff bladder during a blood pressure measurement. The volume of air within the bladder can impact the strength of the monitored oscillation signals and correspondingly impact the accuracy of a NIBP measurement.

One problem with conventional NIBP systems is that the process of wrapping the pressure cuff to a limb is operator sensitive. A first operator may take a blood pressure determination by tightly wrapping the pressure cuff around a patient's arm and inflating the cuff bladder with a relatively low air volume, whereas a second operator may take a blood pressure determination by loosely wrapping the pressure cuff around a patient's arm and inflating the cuff bladder with a relatively high air volume. This variation in cuff bladder air volume can impact oscillation signal strength such that a resultant NIBP measurement may become imprecise.

Oscillometric blood pressure monitors used on the upper arm utilize a range of cuff types to correctly measure a patient's blood pressure. For example, a patient with and arm circumference of 30 centimeters would require an adult type cuff, while a patient with an arm circumference of 20 centimeters might use a child cuff. It is important that the cuff be chosen to match the patient's arm type.

As previously described, conventional NIBP systems initiate a blood pressure measurement by inflating the pressure cuff above the patient's systolic pressure level. It is therefore necessary to estimate a supra-systolic pressure level for a given patient. Additionally, the initial supra-systolic pressure level estimate should ideally be only slightly greater than the patient's actual systolic pressure level. If, for example, a supra-systolic estimate surpasses the patient's actual systolic pressure level by an excessive amount, the duration of the NIBP determination may be unnecessarily prolonged and the pressure cuff may cause pain or discomfort during initial inflation.

Another problem with conventional NIBP systems is that it is difficult to precisely estimate a supra-systolic pressure level that only slightly exceeds a patient's actual systolic pressure level for each of a variety of different patients. Since a child typically has a lower blood pressure than an adult, knowledge of the cuff type could allow better choice of the initial target pressure.

BRIEF DESCRIPTION OF THE INVENTION

The above-mentioned shortcomings, disadvantages and problems are addressed herein which will be understood by reading and understanding the following specification.

In an embodiment, a non-invasive blood pressure monitoring system includes a pressure cuff comprising a resistive portion and a conductive portion aligned with the resistive portion. The non-invasive blood pressure monitoring system also includes a controller operatively connected to the pressure cuff. The controller is adapted to estimate the circumference of the pressure cuff based on the position of the conductive portion relative to the resistive portion.

In another embodiment, a non-invasive blood pressure monitoring system includes a pressure cuff comprising a resistive portion and a conductive portion. The conductive portion is positioned to engage the resistive portion as the pressure cuff is applied to a limb and to thereby form a closed circuit having a variable resistance that is proportional to the circumference of the pressure cuff. The non-invasive blood pressure monitoring system also includes a controller operatively connected to the pressure cuff. The controller is adapted to estimate the circumference of the pressure cuff based on the resistance of the closed circuit.

In yet another embodiment, a pressure cuff includes a resistive portion, a conductive portion aligned with the resistive portion, a first conductor connected to the resistive portion, and a second conductor connected to the conductive portion. The resistive portion, the conductive portion, the first conductor and the second conductor are configured to form a closed circuit when the pressure cuff is applied to a limb. The closed circuit has a variable resistance that is proportional to the circumference of the pressure cuff.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
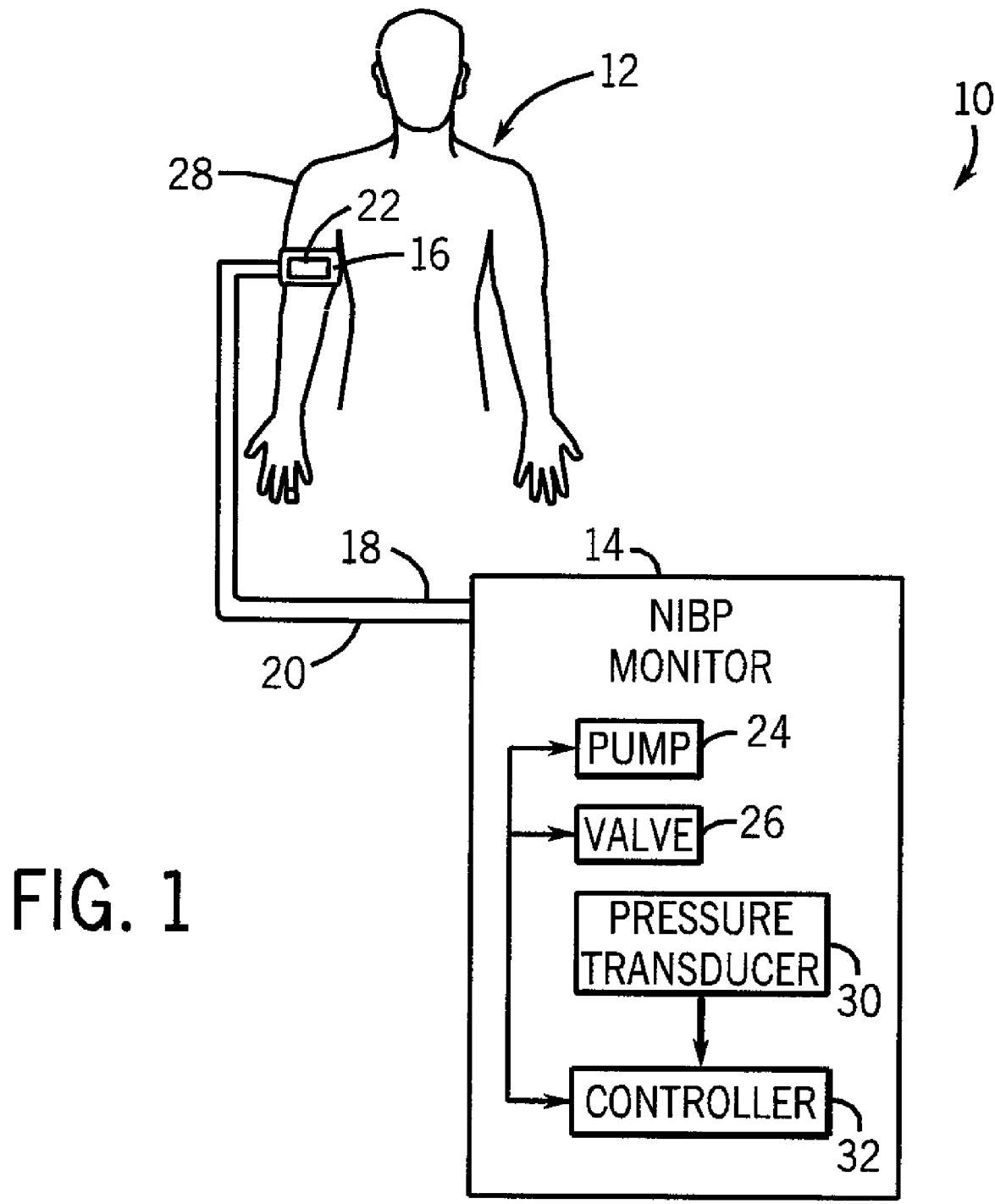
FIG. 1 is a schematic diagram of a non-invasive blood pressure monitoring system attached to a patient in accordance with an embodiment.

Referring to FIG. 1, a non-invasive blood pressure (NIBP) monitoring system 10 attached to a patient 12 is shown in accordance with an embodiment. The NIBP monitoring system 10 includes a NIBP monitor 14 connected to a pressure cuff 16 via the flexible tubes 18, 20. The pressure cuff 16 includes an inflatable cuff bladder 22. Although the cuff bladder 22 is shown as being an integral component of the pressure cuff 16, it should be appreciated that alternate pressure cuff configurations may include a separate cuff bladder. The NIBP monitor 14 includes a pump 24 adapted to inflate the cuff bladder 22, and one or more valves 26 adapted to deflate the cuff bladder 22. The pressure cuff 16 is generally wrapped around a limb 28. The limb 28 is depicted in FIG. 1 as comprising the patient's upper arm, however it should be appreciated that the pressure cuff 16 may alternatively be applied to other locations (e.g., forearm) and other limbs. The NIBP monitor 14 includes a pressure transducer 30 operable to sense or identify pressure pulses at the portion of the limb 28 to which the cuff 16 is attached. A controller 32 converts the pressure pulse data from the pressure transducer 30 into blood pressure data.

The NIBP monitor 14 is configured to measure mean arterial pressure (MAP), systolic blood pressure (SBP), and/or diastolic blood pressure (DBP) by inflating the pressure cuff 16 to a supra-systolic pressure level and measuring oscillations under the cuff 16 as the cuff 16 is deflated. For purposes of this disclosure, the term "oscillation" refers to a measurable pressure level pulse produced by a change in volume of an artery under the pressure cuff 16.

Figure 2:
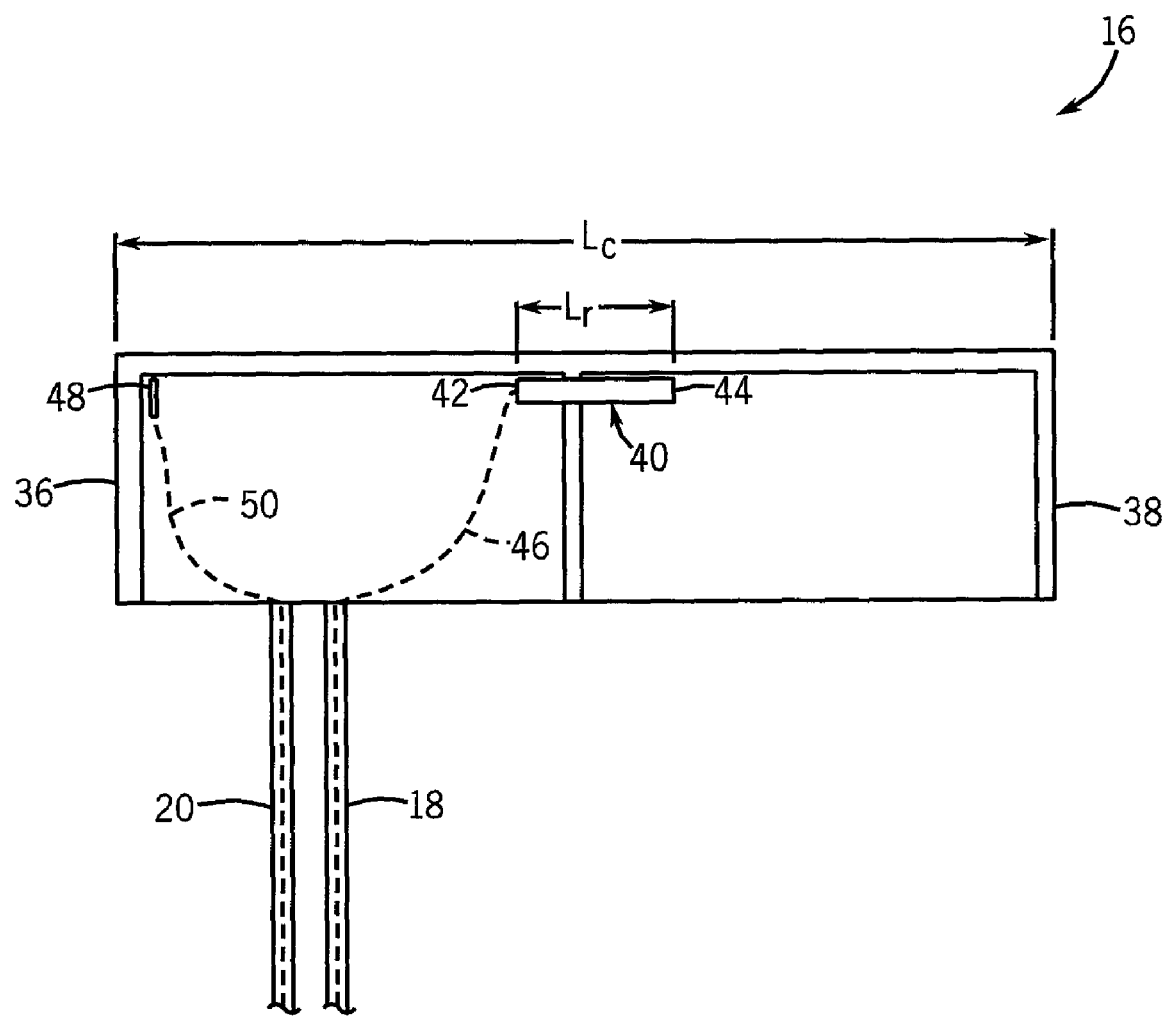
FIG. 2 is a schematic diagram of a pressure cuff in accordance with an embodiment.

Referring to FIG. 2, a schematic illustration of the pressure cuff 16 is shown in accordance with an embodiment. The pressure cuff 16 is generally rectangular and defines a length Lc, a cuff end 36 and a generally opposite cuff end 38. The length Lc is preferably long enough to allow the cuff 16 to be wrapped around a limb such that the cuff ends 36, 38 overlap each other by an amount necessary to secure the pressure cuff 16 to the limb. When wrapped around a limb in the manner described, the generally rectangular pressure cuff 16 becomes generally cylindrical thereby defining a circumference C (shown in FIG. 4). It should be appreciated that pressure cuffs come in a variety of different types in order to accommodated different limbs. Accordingly, a pressure cuff adapted to accommodate an adult's thigh is significantly larger than a pressure cuff adapted to accommodate a child's arm. The pressure cuff 16 may also be made in shapes other than rectangular to accommodate a variety of different limb shapes such as, for example, non-cylindrical limbs.

The pressure cuff 16 includes a resistive portion 40. The resistive portion 40 will hereinafter be described as a generally rectangular strip of resistive material configured to extend lengthwise in a circumferential direction about a limb to be measured. It should, however, be appreciated that the resistive portion 40 may alternatively comprise other shapes and/or be disposed in other orientations. The resistive portion 40 defines a length Lr, a first end 42 and a generally opposite second end 44. The resistive portion 40 is coupled with the controller 32 (shown in FIG. 1) via a conductor 46.

The pressure cuff 16 includes a conductive portion such as the wiper 48 that is preferably disposed on the exterior surface of the cuff near the cuff end 36. The wiper 48 comprises a generally conductive material. The wiper 48 is coupled with the controller 32 (shown in FIG. 1) via a conductor 50.

Figure 3:
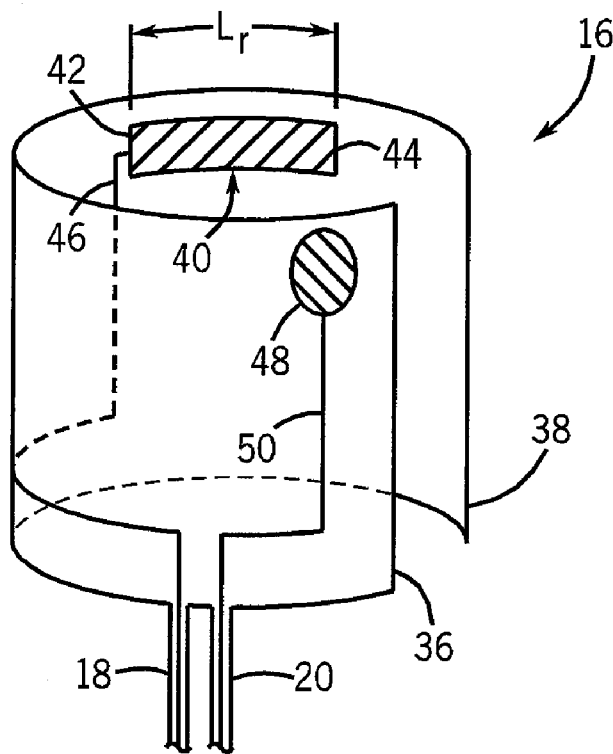
FIG. 3 is a schematic diagram of the pressure cuff of FIG. 2 shown in a partially wrapped position.
Figure 4:
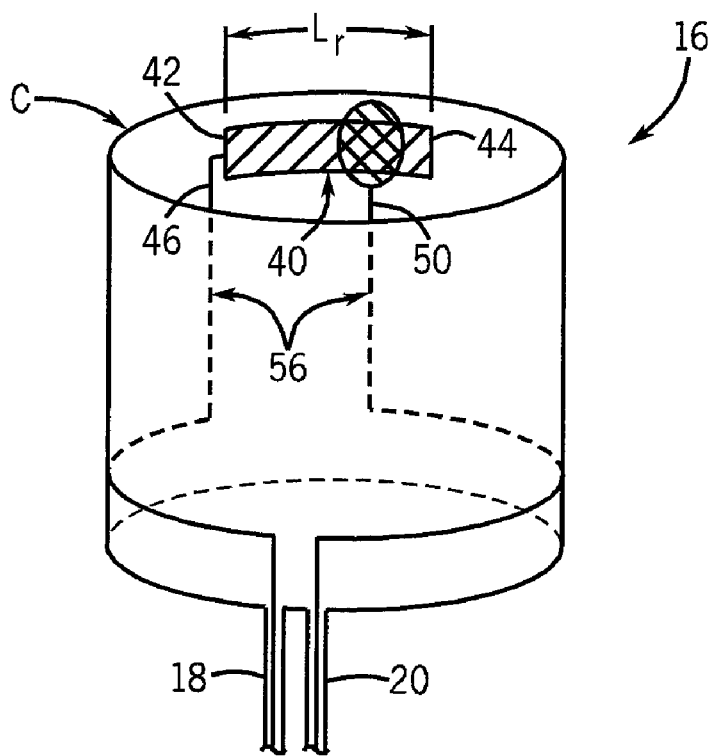
FIG. 4 is a schematic diagram of the pressure cuff of FIG. 3 shown in a more fully wrapped position.

Referring to FIGS. 3 and 4, the pressure cuff 16 is shown initially in a partially wrapped position and thereafter in a more fully wrapped position. As the pressure cuff 16 is being wrapped around a limb, the cuff end 36 overlaps the cuff end 38 such that the wiper 48 is brought into contact with (or into close proximity to) the resistive portion 40. The degree of cuff end 36, 38 overlap dictates the position along the length Lr at which the resistive portion 40 is engaged by the wiper 48. For example, if the cuff ends 36, 38 overlap by relatively greater amount, the wiper 48 will engage the resistive portion 40 closer to the first end 42. Similarly, if the cuff ends 36, 38 overlap by relatively lesser amount, the wiper 48 will engage the resistive portion 40 closer to the second end 44.

When the wiper 48 is brought into contact with the resistive portion 40, a variable resistance closed circuit 56 is formed by the following components: the conductor 50; the wiper 48; the resistive portion 40; and the conductor 46. The amount of resistance in the closed circuit 56 is dictated by position along the length Lr at which the wiper 48 engages the resistive portion 40. As an example, the closed circuit 56 has greater resistance if the wiper 48 engages the resistive portion 40 nearer the second end 44, and the closed circuit 56 has less resistance if the wiper 48 engages the resistive portion 40 nearer the first end 42. The position along the length Lr at which the wiper 48 engages the resistive portion 40 is indicative of the circumference of the pressure cuff 16 and the degree of cuff end 36, 38 overlap. Therefore, by measuring the resistance through the closed circuit 56, the controller 32 can estimate the circumference of the pressure cuff 16 and the degree of cuff end 36, 38 overlap. The pressure cuff circumference information may be implemented, for example, to increase the precision of a NIBP measurement, to decrease the duration of a NIBP measurement, and to minimize discomfort associated with the over-inflation of the pressure cuff 16.

In addition to estimating pressure cuff circumference and the degree of cuff end overlap, it may also be desirable to determine the type of pressure cuff (e.g., child cuff, adult cuff, thigh cuff, etc.) being implemented. It should be appreciated that each cuff type defines a generally unique range of circumferential values over which the cuff remains appropriately sized. These circumferential ranges can be compiled in a convenient form such as, for example, in a table. After the circumference of a given pressure cuff is estimated in the manner previously described, the estimated circumference value can be indexed or compared with the compiled circumferential range data to determine cuff type. Alternatively, each pressure cuff type may be designed to include a generally unique range of resistances over which the specific cuff type remains appropriately sized. This may, for example, by accomplished by providing a different fixed resistor (not shown) for each cuff type, and by disposing the fixed resistors between the wiper 48 and the conductor 50 of an appropriate cuff. The resistance ranges can be compiled and indexed to identify cuff type based on a measured resistance value.

According to one embodiment, the resistive portion 40 is dimensioned and positioned to provide pressure cuff sizing feedback. More precisely, the resistive portion 40 may be dimensioned and positioned such that the first and second ends 42, 44 define range marks designating the minimum and maximum patient limb circumference for which the pressure cuff 16 is appropriate. If the cuff ends 36, 38 overlap to the extent that the wiper 48 passes beyond the first end 42, the pressure cuff 16 is too large for the limb to be measured and the closed circuit 56 of FIG. 4 cannot be formed. Similarly, if the cuff ends 36, 38 overlap by an amount that is insufficient to bring the wiper 48 into contact with the second end 44, the pressure cuff 16 is too small for the limb to be measured and closed circuit 56 of FIG. 4 cannot be formed. Accordingly, the controller 32 (shown in FIG. 1) may be configured to recognize when the closed circuit 56 has not been formed because of excessive or insufficient cuff end 36, 38 overlap, and to thereafter indicate that the pressure cuff 16 is improperly sized. Alternatively, the resistive portion 40 can be dimensioned and positioned to extend beyond the range marks such that improper cuff sizing is indicated by a measured resistance value falling outside a predefined acceptable resistance range.

While the invention has been described with reference to preferred embodiments, those skilled in the art will appreciate that certain substitutions, alterations and omissions may be made to the embodiments without departing from the spirit of the invention. Accordingly, the foregoing description is meant to be exemplary only, and should not limit the scope of the invention as set forth in the following claims.

We claim:

1. A non-invasive blood pressure monitoring system comprising:
   a pressure cuff configured to surround a limb of a patient and having an adjustable circumference;
   a single continuous strip of resistive material attached to the pressure cuff and positioned to extend lengthwise in a circumferential direction about the limb of the patient when the pressure cuff is positioned on the patient, the strip of resistive material extending between a first end and a second end;
   a conductive portion attached to the pressure cuff and positioned to engage the strip of resistive material when the pressure cuff is applied to the limb of the patient; and
   a controller operatively connected to the strip of resistive material and the conductive portion of the pressure cuff, wherein the controller is adapted to estimate the circumference of the pressure cuff based upon the position of the conductive portion along the length of the strip of resistive material between the first and second ends.

2. The non-invasive blood pressure monitoring system of claim 1, wherein the controller is adapted to determine whether the pressure cuff is appropriately sized for a limb based on the position of the conductive portion relative to the strip of resistive material.

3. The non-invasive blood pressure monitoring system of claim 1, wherein said first and second ends indicate a minimum and maximum limb circumference for which the pressure cuff is appropriate.

4. The non-invasive blood pressure monitoring system of claim 1, wherein the conductive portion comprises a wiper.

5. The non-invasive blood pressure monitoring system of claim 1, wherein the conductive portion is positioned to engage the strip of resistive material as the pressure cuff is applied to a limb and to thereby form a closed circuit having a variable resistance that is proportional to the circumference of the pressure cuff.

6. The non-invasive blood pressure monitoring system of claim 1, wherein the controller is adapted to identify a pressure cuff type based on the position of the conductive portion relative to the strip of resistive material.

7. The non-invasive blood pressure monitoring system of claim 6, wherein the pressure cuff further comprises a resistor coupled with one of the strip of resistive material and the conductive portion, said resistor being adapted to facilitate the identification of the pressure cuff type.

8. A non-invasive blood pressure monitoring system comprising:
   a pressure cuff comprising:
      a single continuous strip of resistive material attached to the pressure cuff and configured to extend lengthwise in a circumferential direction about a limb, the continuous strip of resistive material extending between a first end and a second end; and
      a conductive portion positioned to engage the continuous strip of resistive material between the first and second ends as the pressure cuff is applied to a limb and to thereby form a closed circuit having a variable resistance that is proportional to the circumference of the pressure cuff; and
   a controller operatively connected to the single resistive strip and the conductive portion of the pressure cuff, wherein said controller is adapted to estimate the circumference of the pressure cuff based on the resistance of the closed circuit.

9. The non-invasive blood pressure monitoring system of claim 8, wherein the controller is adapted to determine whether the pressure cuff is appropriately sized for a limb.

10. The non-invasive blood pressure monitoring system of claim 8, wherein the first and second ends of the continuous strip of resistive material indicate a minimum and maximum limb circumference for which the pressure cuff is appropriate.

11. The non-invasive blood pressure monitoring system of claim 8, wherein the conductive portion comprises a wiper.

12. The non-invasive blood pressure monitoring system of claim 8, wherein the controller is adapted to identify a pressure cuff type based on the resistance of the closed circuit.

13. The non-invasive blood pressure monitoring system of claim 12, wherein the pressure cuff further comprises a resistor coupled with one of the strip of resistive material and the conductive portion, said resistor being adapted to facilitate the identification of the pressure cuff type.

14. A pressure cuff comprising:
   a single continuous strip of resistive material attached to the pressure cuff and configured to extend lengthwise in a circumferential direction about a limb, the continuous strip of resistive material extending between a first end and a second end;
   a conductive portion aligned with the strip of resistive material;
   a first conductor connected to the strip of resistive material; and
   a second conductor connected to the conductive portion;
   wherein the single continuous strip of resistive material, the conductive portion, the first conductor and the second conductor are configured to form a closed circuit when the pressure cuff is applied to a limb, said closed circuit having a variable resistance that is proportional to the circumference of the pressure cuff.

15. The pressure cuff of claim 14, wherein the first and second ends indicate a minimum and maximum limb circumference for which the pressure cuff is appropriate.

16. The pressure cuff of claim 14, wherein the conductive portion comprises a wiper.

17. The pressure cuff of claim 14, further comprising a resistor coupled with one of the resistive portion and the conductive portion.

* * * * *